United States Patent
Heeter et al.

(10) Patent No.: US 9,321,029 B2
(45) Date of Patent: Apr. 26, 2016

(54) STYRENE REMOVAL IN PARAXYLENE RECOVERY PROCESS

(71) Applicant: ExxonMobil Chemical Patents Inc., Baytown, TX (US)

(72) Inventors: Glenn A. Heeter, The Woodlands, TX (US); John D. Ou, Houston, TX (US); Allen S. Gawlik, Houston, TX (US); Terrance C. Osby, Manvel, TX (US); Jeevan S. Abichandani, Houston, TX (US); Robert G. Tinger, Friendswood, TX (US); Indulis J. Eilands, League City, TX (US); Shifang L. Luo, Annandale, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/849,918

(22) Filed: Sep. 10, 2015

(65) Prior Publication Data

US 2015/0375195 A1 Dec. 31, 2015

Related U.S. Application Data

(62) Division of application No. 13/875,373, filed on May 2, 2013, now Pat. No. 9,156,749.

(60) Provisional application No. 61/681,486, filed on Aug. 9, 2012, provisional application No. 61/653,688, filed on May 31, 2012.

(51) Int. Cl.
*B01J 19/24* (2006.01)
*C07C 7/13* (2006.01)
*C07C 7/148* (2006.01)
*C07C 2/86* (2006.01)

(52) U.S. Cl.
CPC .............. *B01J 19/24* (2013.01); *B01J 19/245* (2013.01); *C07C 2/864* (2013.01); *C07C 2/865* (2013.01); *C07C 7/13* (2013.01); *C07C 7/148* (2013.01); *B01J 2219/00006* (2013.01); *B01J 2219/24* (2013.01); *C07C 2529/40* (2013.01); *C07C 2529/70* (2013.01)

(58) Field of Classification Search
None
See application file for complete search history.

(56) References Cited

U.S. PATENT DOCUMENTS

| | | |
|---|---|---|
| 4,795,550 A | 1/1989 | Sachtler et al. |
| 6,005,156 A | 12/1999 | Joly et al. |
| 6,313,362 B1 | 11/2001 | Green et al. |
| 6,423,879 B1 | 7/2002 | Brown et al. |
| 6,504,072 B1 | 1/2003 | Brown et al. |
| 7,199,275 B2 | 4/2007 | Smith |
| 7,731,839 B2 | 6/2010 | Brown et al. |
| 2006/0270886 A1 | 11/2006 | Brown et al. |
| 2010/0305378 A1 | 12/2010 | Galloway, Jr. et al. |
| 2011/0263918 A1 | 10/2011 | Ou et al. |
| 2012/0316375 A1 | 12/2012 | Zheng et al. |

FOREIGN PATENT DOCUMENTS

| | | |
|---|---|---|
| FR | 2 295 935 | 7/1976 |
| JP | 51-26421 | 8/1976 |
| JP | 02-138137 | 5/1990 |
| WO | WO 99/38823 | 8/1999 |
| WO | WO 99/38936 | 8/1999 |
| WO | WO 00/35863 | 6/2000 |
| WO | WO 01/56960 | 8/2001 |
| WO | WO 2004/085352 | 10/2004 |
| WO | WO 2010/120616 | 10/2010 |
| WO | WO 2011/031579 | 3/2011 |

OTHER PUBLICATIONS

U.S. Appl. No. 61/653,698, filed May 31, 2012, Heeter et al.

*Primary Examiner* — Tam M Nguyen

(57) ABSTRACT

The invention relates to removal of styrene from hydrocarbon mixtures, and more particularly, removal of styrene from hydrocarbon mixtures containing higher than equilibrium paraxylene concentrations.

4 Claims, 4 Drawing Sheets

STYRENE REMOVAL IN PARAXYLENE RECOVERY PROCESS

CROSS REFERENCE TO RELATED APPLICATIONS

This application is a divisional of and claims priority to and the benefit of U.S. patent application Ser. No. 13/875,373, filed May 2, 2013, now U.S. Pat. No. 9,156,749, and U.S. Provisional Application No. 61/681,486, filed on Aug. 9, 2012, and U.S. Provisional Application No. 61/653,688, filed on May 31, 2012, the disclosures of which are incorporated herein by reference in their entirety.

FIELD OF THE INVENTION

The invention relates to purification of process streams in the production of paraxylene by alkylation of benzene and/or toluene and to the removal of styrene from aromatic hydrocarbon streams containing higher than equilibrium concentrations of paraxylene.

BACKGROUND OF THE INVENTION

Of the aromatic C8 isomers, including the three xylene isomers and ethylbenzene, paraxylene is of particularly high value since paraxylene is useful in the manufacture of synthetic fibers and resins. Refinery and chemical plant streams containing the aromatic C8 isomers typically contain, at thermodynamic equilibrium, only about 22-24 wt % paraxylene, based on the weight of the xylene isomers in the stream. Separation of paraxylene from the other C8 isomers requires superfractionation and/or multistage refrigeration steps and/or adsorptive separation, all of which are energy intensive. There is a need to provide processes for producing paraxylene in more efficient ways, such as in higher selectivity than can be obtained from refinery and chemical plant streams.

One known method for producing paraxylene selectively involves the alkylation of toluene and/or benzene with methanol and/or DME (dimethylether) over a solid acid catalyst. Selectivities to paraxylene in excess of 90 wt % (based on total C8 aromatic product) have been reported by reacting toluene with methanol in the presence of a catalyst comprising a porous crystalline material, preferably a medium-pore zeolite and particularly ZSM-5, having a Diffusion Parameter for 2,2-dimethylbutane of about 0.1-15 sec$^{-1}$ when measured at a temperature of 120° C. and a 2,2-dimethylbutane pressure of 60 torr (8 kPa). See U.S. Pat. Nos. 6,423,879 and 6,504,072.

WO 99/38823 reported a reactive distillation process comprising the contact of toluene with a methylating agent in the presence of a zeolite in a reaction/distillation column produces, as a side product, DME, which can be recycled (with unreacted methanol) to extinction in the process. The process operates at no greater than 320° C.

It has recently been discovered that the alkylation of benzene and/or toluene with methanol can also result in the production of a variety of oxygenates, in addition to DME, but also other oxygenate by-products. See for instance U.S. patent application Ser. No. 13/487,651. According to the invention described in Ser. No. 13/487,651, the concentration of phenolic impurities in a xylene stream produced by alkylation of benzene and/or toluene with methanol can be reduced to trace levels, e.g., below 0.1 ppmw, by one or more washing treatments with an aqueous solution of a base. The resultant treated xylene stream, if necessary after water washing to remove any phenate-containing solution, can then be recycled to the xylene splitter to generate additional paraxylene or can be used as a solvent.

Recently, a process for the production of paraxylene selectively by: (i) reacting of toluene and/or benzene with methanol in the presence of a suitable catalyst under appropriate conditions to process stream comprising paraxylene in higher than equilibrium amounts; (ii) contact of said process stream comprising paraxylene in higher than equilibrium amounts with a suitable adsorbent to remove phenol, said phenol having been produced in (i), or is present in the feedstream of toluene and/or benzene and/or alkylating agent (methanol and/or DME), or any combination thereof, to provide a product stream having a lower concentration of phenol than said process stream, has been described in U.S. Provisional Patent Application No. 61/653,698.

It has also recently been discovered that xylenes produced by alkylating toluene and/or benzene with an alkylating agent comprising methanol and/or DME over a solid acid catalyst contain small quantities of styrene, which, if not removed, could cause operability problems for downstream paraxylene recovery processes, or even further, in processes using paraxylene, such as the production of terephthalic acid, and derivatives thereof, including polyester fibers, films, and the like.

Several characteristics of the xylene produced in this manner make styrene removal challenging. The desired product, paraxylene, is present at higher-than-equilibrium concentration. The catalyst used to remove styrene must therefore show minimal xylenes isomerization activity. The catalyst must also minimize formation of benzene, which also can have detrimental effects on downstream processing. Furthermore, as already mentioned, the product contains a variety of oxygenates, such as phenol. Moreover, olefinic compounds may enter the alkylation reaction system via the feedstream of toluene such as catalytic reforming units, which are a source of toluene for the aforementioned alkylation reaction. These and other problems make the treatment of the product stream from the alkylation of benzene and/or toluene in the presence of an acid catalyst difficult.

U.S. Pat. No. 4,795,550 teaches converting trace quantities of olefinic impurities to nonolefinic hydrocarbons by contacting an aromatic process stream from an alkylation reaction with a solid catalyst composite comprising a crystalline aluminosilicate zeolite and a refractory inorganic oxide. Faujasite is mentioned as a preferred aluminosilicate zeolite and the refractory inorganic oxide can be alumina, silica-alumina, or a mixture of both.

U.S. Pat. No. 6,313,362 teaches that in an alkylation/transalkylation process, an aromatic alkylation process stream comprising polyalkylated aromatic compounds is contacted with a purification medium in a liquid phase pre-reaction step, prior to transalkylation, to remove impurities, including styrene. A large pore molecular sieve catalyst such as MCM-22 may be used as the purification medium in the pre-reaction step because of its high reactivity for alkylation, strong retention of catalyst poison and low reactivity for oligomerization under the pre-reactor conditions. The alkylation processes envisioned include the production of ethylbenzene, cumene, ethyltoluene, and cymenes.

U.S. Pat. No. 7,731,839 teaches treating an aromatic hydrocarbon feedstock having undesirable olefins including styrene with a catalyst such as MCM-22 to reduce the amount of undesirable olefins. Likewise, U.S. Pat. No. 6,005,156 teaches a process for the reduction of olefins and diolefins from mixtures of aromatic hydrocarbon-rich cuts by treatment in a hydrogenation zone and then treatment with clay.

Although many sources of aromatic-rich hydrocarbon cuts are mentioned, a process for alkylation of benzene and/or toluene with methanol is not recognized. Similarly, U.S. Pat. No. 7,199,275 teaches treatment of a partially dehydrated aromatic feedstock containing styrene as an impurity by contacting with a first molecular sieve having a Si/Al molar ratio less than about 5 and a second molecular sieve having a Si/Al molar ratio of greater than about 5. The thus-treated feedstock is then used for an alkylation reaction of benzene with ethylene and/or propylene or translkylation reactions in the liquid phase.

Other references include FR 2295935, teaching the reduction of olefin and diene content of an aromatics-rich fraction by subjecting the fraction to an acid-catalyzed vapor or liquid-phase alkylation reaction; JP 2138137A, teaching separation of styrene from a C8 aromatics stream by selective adsorption of styrene with a modified faujasite zeolite; and JP 76026421B, teaching isolating styrene from a hydrocarbon fraction comprising styrene and ethylbenzene and/or xylene isomers by adsorption of styrene with a zeolite comprising an alkali or alkaline earth metal.

As far as the present inventors are aware, the prior art has not addressed the problem of styrene impurities in a system for alkylation of benzene and/or toluene with an alkylating agent selected from methanol, DME, and mixtures thereof, in the presence of a catalyst to produce a process stream comprising higher than equilibrium amounts of paraxylene and with the co-production of styrene.

The present inventors have surprisingly discovered a method of purifying said process stream of styrene impurities without significant loss of the desired paraxylene product or co-production of additional impurities.

SUMMARY OF THE INVENTION

The invention is directed to the purification of an aromatic hydrocarbon stream including selective removal of styrene from a process stream, said process comprising the contact of benzene and/or toluene with an alkylating agent, in the presence of a suitable alkylation catalyst under appropriate conditions to selectively produce paraxylene, said selective removal of styrene comprising the contact of said process stream with a suitable material under conditions effective to provide a product stream from said process, said product stream having a lower concentration of styrene than said process stream, preferably less than 30 ppm, more preferably less than 20 ppm. The alkylating agent is preferably selected from methanol, dimethylether (DME) and mixtures thereof.

The process stream treated to provide a lower concentration of styrene may be the feedstream to the process, such as the toluene stream from a catalytic reforming unit, or a stream comprising xylenes downstream of the alkylation reactor, such as upstream of a fractionator used to separate unreacted toluene (e.g., "detol fractionator") and/or methanol from the alkylation reactor product xylene stream, the bottoms and/or overhead product from said detol fractionator, a xylenes splitter, such as utilized to separate heavy aromatics (C9+ aromatic hydrocarbons) from the xylene product, upstream or downstream from a paraxylene recovery unit (e.g., adsorptive separation, such as a Parex™ adsorptive separation unit or Eluxyl™ adsorptive separation unit, or a crystallization apparatus), upstream or downstream of an isomerization unit (which may be a liquid phase or vapor phase isomerization unit, in series or parallel), and the like. The process stream may also comprise an imported process stream or any other type of stream which has picked up styrenic impurities, particularly styrene such as from a previous cargo.

The process is also directed to a process for the production of paraxylene selectively by: (i) reacting of toluene and/or benzene with methanol and/or DME in the presence of a suitable alkylation catalyst under appropriate conditions to produce a process stream comprising paraxylene in higher than equilibrium amounts and styrene; (ii) contact of said process stream comprising paraxylene in higher than equilibrium amounts and styrene with a suitable material to remove at least some of said styrene and provide a product stream having lower concentration of styrene than said process stream.

By "selectively produce paraxylene" is meant the production of xylenes wherein paraxylene is present in amounts greater than is present in an equilibrium mixture of C8 aromatic isomers, and by "equilibrium mixture" or "equilibrium amounts" with reference to the concentration of paraxylene in a mixture of C8 aromatic isomers is meant generally about 22-24 wt %. Preferably the alkylation reaction produces a product stream having at least 70 wt %, such as 75 wt %, 80 wt %, 85 wt %, 90 wt %, (all wt % herein based on the total amount of C8 aromatic isomers unless otherwise specified), to about 99 wt % or even higher, particularly in the ranges of 70-90 wt %, 75-88 wt %, 80-95 wt %, 82-88 wt %, or in the range of from any lower wt % disclosed to any higher wt % disclosed.

In embodiments the amount of styrene present after said contact with a catalyst suitable for selective removal of styrene is less than 20 ppm wt, more preferably less than 10 ppm wt. based on the total amount of aromatic hydrocarbon.

By "selective removal of styrene" means that the amount of styrene removed in the styrene-removal contacting step is, in embodiments, equal to or greater than the amount of styrene produced in the alkylation reaction, or so that the final product after the styrene removal step is less than 20 ppm, or less than 10 ppm, and/or greater than the amount of benzene produced in said step, and/or greater than the amount of paraxylene isomerization that occurs in said styrene removal step.

In embodiments said process stream may be subjected to additional process steps such as fractionation, adsorptive separations, crystallization, membrane separation, and the like, to remove species other than phenol.

In embodiments, said contact may be in the presence of hydrogen or it can be in the absence of hydrogen.

In embodiment said contact occurs in the temperature range of 100 to 275° C., more preferably 103 to 180° C.

In embodiments the production of benzene in said styrene removal step is in amounts of 30 ppm wt. or less based on the total amount of aromatic hydrocarbon, and/or the amount of paraxylene isomerization is less than 1 wt %, based on the amount of paraxylene.

In embodiments the material used in the styrene removal step is selected from MWW molecular sieves, clay, and mixtures thereof, such as at least one of MCM-22, MCM-36, MCM-49, MCM-56, EMM-10 molecular sieves, and Engelhard F-24, Filtrol 24, Filtrol 25, and Filtrol 62 clays, Attapulgus clay and Tonsil clay. The molecular sieves have been described in numerous patents and publications, such as U.S. Pat. Nos. 4,954,325; 5,229,341; 5,236,575; and 5,362,697, and the clays are likewise well-known. Any of these are commercially available.

It is an object of the invention to provide a continuous, semi-continuous, or batch process of purifying xylene feedstream of styrene impurities with minimal co-production of benzene and minimal isomerization of paraxylene to another C8 aromatic isomer.

It is another object of the invention to provide an apparatus adapted for the process of the invention.

These and other objects, features, and advantages will become apparent as reference is made to the following detailed description, preferred embodiments, examples, and appended claims.

DETAILED DESCRIPTION

According to the invention, xylenes produced by alkylating toluene and/or benzene with methanol and/or dimethylether (DME) with a catalyst such as a solid acid catalyst contain small quantities of styrene, which, if not removed, could cause operability problems for downstream para-xylene recovery processes. The invention is a method of removing the styrene by contact with an appropriate material under conditions sufficient to reduce the amount of styrene without production of significant amount benzene and/or isomerization of paraxylene, and also to apparatus adapted for said process.

Without wishing to be bound by theory, in embodiments, it is believed that styrene is converting to a heavy aromatic product (e.g., C9 aromatics) over said catalyst under appropriate conditions to reduce the amount of styrene without production of significant amounts of benzene or isomerization of paraxylene. The heavy product could then be removed in downstream distillation.

The invention may also be practiced using a feedstream of benzene, toluene, or any combination thereof, as the aromatic species to be alkylated, and a feedstream of methanol, dimethylether (DME), and any combination thereof, as the alkylating agent.

A typical composition of xylenes produced from the reaction of toluene with methanol in the presence of a solid acid catalyst is shown in Table 1.

TABLE 1

| Compound | wt % |
| --- | --- |
| Toluene | 0.0950 |
| Styrene | 0.0648 |
| mixed xylenes | 94.56 |
| Ethylbenzene | 0.47 |
| C9 aromatics | 4.7574 |
| phenol | 0.0014 |
| Other oxygenates | >0.05 |

Representative species found in the product include 1,2,4-trimethylbenzene, 1-methyl-4-ethylbenzene, n-nonane, naphthalene, 1,4-dimethyl-2-ethylbenzene, biphenyl, anthracene, C16 aromatic alkylates, benzoic acid, 4-methylbenzoic acid, o-cresol, 2,4-dimethylphenol, and the like. The presence of styrene would typically not be expected in a stream of paraxylene-enriched xylenes (that is, paraxylene in higher than equilibrium amounts).

Figure 1:
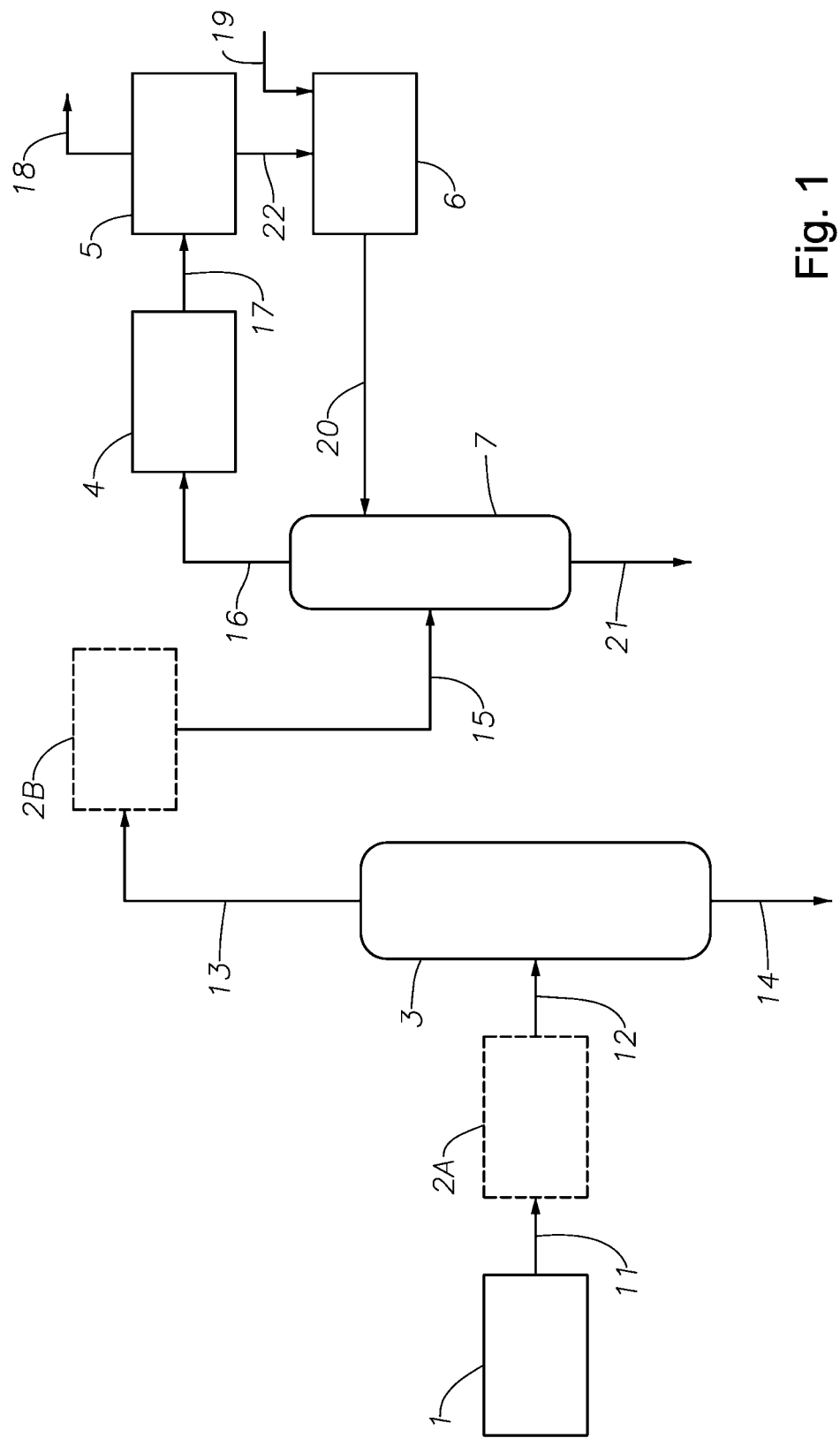
FIGS. 1 and 2 are schematic diagrams showing certain preferred embodiments of the present invention.

The invention may be better understood by reference to FIG. 1, which is a schematic illustration of preferred embodiments of the invention. One of skill in the art in possession of the present discourse will understand that the invention may be practiced other than as specifically illustrated in FIG. 1, and the illustration is not intended to be limiting.

In FIG. 1, apparatus 1 is a reactor suitable for carrying out alkylation of benzene and/or toluene in the presence of a solid acid catalyst, such as ZSM-5, particularly a phosphorus-containing ZSM-5, and more particularly a phosphorus-containing ZSM-5 that has been steamed at temperatures on the order of 1000° F. The specifics of the apparatus 1 do not form a part of the present invention, except as otherwise stated herein, but rather have been described in numerous prior art patents, patent application, and publications.

The effluent from 1, which is an aromatic hydrocarbon stream rich in paraxylene, such as 70 wt % or more, as described in more detail herein, a typical composition of which is shown in Table 1, above, is passed via conduit 11 to styrene removal unit 2A. The unit 2A is illustrated with dotted lines since it is but one possible placement of such a unit, albeit preferred, according to embodiments of the invention. The styrene-depleted stream rich in paraxylene is passed via conduit 12 to a fractionation column or splitter 3 wherein the stream is split into a paraxylene-enriched overhead passed downstream in the process through conduit 13 and a paraxylene depleted bottoms product passed downstream in the process through conduit 14.

Styrene removal unit 2B illustrates a second possible placement of a styrene removal unit according to the present invention. One or both of 2A and 2B may be used in an embodiment of the process according to the invention. Styrene removal units may comprise one or more vessels containing, by way of example, MCM-22. Such units are per se known in the art.

The paraxylene-enriched overhead from splitter 3, is passed via conduit 15 to an optional second fractionation column 7, or in the case where unit 2A is not present, a first styrene removal unit 2B. The paraxylene-enriched stream 15, now having been treated by one or both of styrene removal units 2A and/or 2B is then passed via conduit 15 to fractionator 7 to remove heavies such as aromatic C9+s 21 and pass an overhead 16, comprising a paraxylene-enriched, styrene-depleted stream (relative to effluent 11), further downstream in the process. This stream 16 may optionally be treated in apparatus 4 to remove other impurities, such as oxygenates, e.g., by an absorbent-based phenol adsorption and/or such as by a caustic wash. See, for instance, U.S. Provisional Patent Application No. 61/653,698 and U.S. patent application Ser. No. 13/487,651. The stream 17 is then sent to paraxylene removal unit 5 of the type known in the art, such as an adsorptive separation unit (e.g., Parex unit or Eluxyl unit) or separation by crystallization. The final desired high purity paraxylene stream is taken off via conduit 18 and the paraxylene-depleted stream 22, otherwise known as raffinate with respect to paraxylene removal units, is sent to a liquid phase isomerization unit 6, of the type well-known in the art, wherein the paraxylene-depleted raffinate is isomerized to equilibrium concentration xylenes (i.e., about 22-24 wt % paraxylene). The isomerization may be liquid phase or vapor phase, both per se known in the art. After isomerization the equilibrium xylenes stream may be recycled via line 20 to fractionator 7 or otherwise processed as desired.

Figure 2:
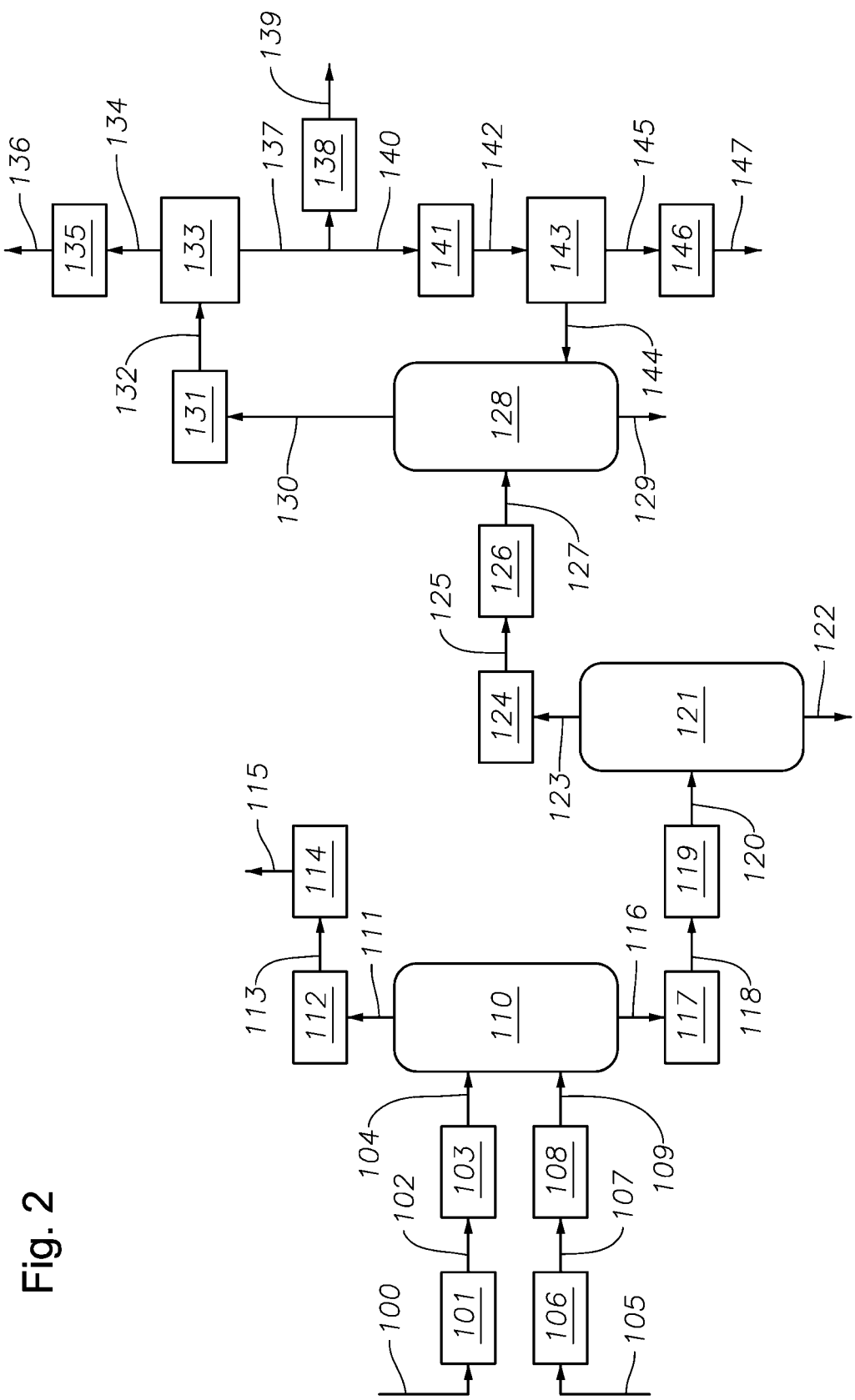

The invention may be still be even better understood by reference to FIG. 2, which is a schematic illustration of another preferred embodiment of the invention. One of skill in the art in possession of the present discourse will understand that the invention may be practiced other than as specifically illustrated in either FIG. 1 or 2, and the illustrations is not intended to be limiting.

FIG. 2 illustrates apparatus downstream of the alkylation reactor, not shown for convenience of view. In FIG. 2, fresh feed 100, comprising alkylating agents selected from methanol, DME, or a combination thereof, and/or the aromatic species to be alkylated, selected from benzene, toluene, and mixtures thereof, are passed through phenol-removal unit 101 and then via conduit 102 to styrene-removal unit 103, and then through conduit 104 to fractionator 110, which removes toluene overhead to be sent to the alkylation reactor, as described further hereinbelow. One of the advantages of the present invention is that one or more of extracted toluene and non-extracted toluene may be used, and since numerous sources of toluene can be used in the alkylation reactor using a solid acid catalyst, as well as numerous sources of methanol and/or DME alkylating agent. Thus, it is advantageous to have a pre-treatment of the feed(s) in one or both of units 101 and 103 as set forth in FIG. 2, however use of such pretreatment is optional. It will also be appreciated that the alkylating agent(s) and benzene and/or toluene can be fed separately together, and likewise the choice of whether to have a pre-treatment by one or both of units 101 and 103, in either order, can be made independently on each separate feedstream. Water is advantageously also added to the upstream alkylation reactor and may be added into the system represented by the entirety of the alkylation reactor (not shown) and the apparatus shown in FIG. 2 along with feed 100, or it may be added separately to said system directly to the alkylation reactor; the addition of water and the location of addition is optional. Advantageously, the addition of water into the alkylation reactor is in an amount sufficient to reduce coking of the catalyst. One or more of the feeds may be added preheated and the feed(s) may be added as liquid or vapor to reactor 100.

Continuing with FIG. 2, 105 represents one or more of the recycled reactor products, advantageously previously treated to remove gaseous products (e.g., light olefins) and possibly dried of water, although, as mentioned above, water may be added as part of the feed. The removal of gaseous products and/or water is not shown in FIG. 2 as it does not form a part of the present invention per se, and could be accomplished by one of ordinary skill in the art in possession of the present disclosure. Typically unreacted methanol and/or DME and unreacted benzene and/or toluene are recycled via line 105 or they may be recycled separately, or a combination thereof, and thus pretreatment by phenol-removal unit 106 and/or styrene removal unit 108, fluidly connected to 106 via line 107 and to reactor 110 via line 109, is advantageous.

Continuing with FIG. 2, fractionator tower 110 (or "detol tower") removes toluene overhead and the toluene can optionally be sent via conduit 111 through one or more of phenol removal unit 112 and styrene removal unit 114, fluidly connected by conduit 113, prior to being recycled to the alkylation reactor (again, not shown) via conduit 115. It will be appreciated that the toluene stream 111 may be optionally cooled to a liquid by known methods, not shown, prior to treatment in units 112 and/or 114, and that whether or not to have a phenol removal step and/or styrene removal step between the detol tower 110 and the alkylation reactor, and the order thereof, can be determined independently by one of ordinary skill in the art in possession of the present disclosure.

The bottoms product of detol tower 110, comprising the desired paraxylene-enriched alkylation reactor products, leaves 110 through conduit 116 and may optionally be treated by one or more of the phenol removal unit 117 and/or the styrene removal unit 119, fluidly connected by conduit 118, and is then passed to xylene splitter 121 via conduit 120 to remove heavier products (i.e., C9+ aromatic hydrocarbons) as a bottoms product through conduit 122. The C9+s may be advantageously used with a transalkylation unit integrated with the system shown in FIG. 2, and indeed the entire apparatus shown in FIG. 2, and the alkylation reactor not shown, may be advantageously integrated with other known methods of generating xylenes and/or other aromatic products, for greater efficiency of feedstream use, integration of heat (which in embodiments is generated by the alkylation reactor), and so on.

The overheads 123 from xylene splitter 121 may also optionally be treated by one or both of phenol removal unit 124 and styrene removal unit 126, fluidly connected via conduit 125 prior to being sent via conduit 127 to an optional second xylene splitter 128, which analogous to splitter 121, separates the desired paraxylene-enriched xylenes stream overhead, to conduit 130, from bottoms product 129, which may again be disposed of in the same manner as bottoms product 122.

The overheads 130 may be treated by one or both of a phenol removal unit or styrene removal unit, and in the embodiment of FIG. 2, is illustrated by a single unit 131, which may represent one or more of such units.

The remaining portions of FIG. 2 are similar to the per se well-known xylenes loop, but integrated with the styrene removal step(s) according to the present invention, and thus, the paraxylene-enriched stream 132 is passed to a paraxylene recovery unit 133, which may be an adsorption unit (e.g., Parex adsorption unit or Eluxyl adsorption unit), or a crystallizer unit, or membrane unit, and the like, wherein paraxylene is separated from its C8 aromatic isomers, to yield very high purity paraxylene via conduit 134, which may yet further be treated by one or more of a phenol-removal unit and/or styrene removal unit, represented by a single apparatus 135, to yield a highly pure, highly enriched paraxylene product, having, in embodiments, a paraxylene content of greater than 99.0 wt % (based on the entire content of the stream), and further characterized by one or more of: (i) a styrene content of less than 30 wppm; and (ii) a phenol content of less than 1 wppm.

Finally, continuing with the description of the embodiment shown in FIG. 2, the raffinate (paraxylene-depleted xylenes stream) from the paraxylene removal unit 133, leaving via conduit 137, may be recovered as mixed xylenes 139, optionally but advantageously treated by one or more of a styrene removal unit and/or a phenol removal unit, again represented by a single apparatus 138, and/or via conduit 140 to the isomerization unit represented by apparatus 143, optionally but advantageously treated by one or more of a styrene removal unit and/or a phenol removal unit, again represented by a single apparatus 141 which is fluidly connected to isomerization unit 143 by conduit 142. The product of the isomerization unit, as is well-known, will be an equilibrium stream of xylenes, which may be advantageously then recycled back xylenes splitter 128 and/or sent to ethylbenzene purge (not shown) via conduit 145, optionally treated by one or more of phenol removal and/or styrene removal unit, again represented by a single unit 146, leaving said unit, if present, via conduit 147.

The isomerization unit 143 may be liquid phase or gas phase or both may be used in series or parallel. Both liquid and gas phase isomerization processes and units to use in said processes are per se well-known in the art.

Material that can be used for styrene removal according to the present invention, for example in one or more units 2A and/or 2B such as illustrated schematically in FIG. 1, or one or more of units 103, 108, 115, 119, 126 and also 131, 135, 138, 141, and 146, such as illustrated schematically in FIG. 2, include members of the MWW family of zeolites (MCM-22, MCM-49, MCM-56, etc.), and clays. These zeolites can be produced in various formulations, including those bound with clay, alumina, or silica, and self-bound formulations. Fresh or regenerated catalysts can be used, as well as catalyst that has been reprocessed after use in a different service, such as ethylbenzene or cumene production. Another type of catalyst that could be used for styrene removal from these xylene streams are clays. Catalyst beds that contain mixed layer(s) of clay and MWW family zeolite catalysts could also be used. MWW and methods of making it, molecular formula, and other methods of characterization, are per se well-known in the art; see for instance, U.S. Pat. No. 5,001,295.

In embodiments, the process for styrene removal from xylenes streams produced by the reaction of methanol and benzene and/or toluene by contact with the appropriate catalyst can use fixed-bed, adiabatic reactors operating at temperatures such as from 100-300° C. and WHSV such as from 1.0-100 hr-1, preferably with pressure high enough to maintain liquid-phase conditions.

Phenol removal, which is the subject of U.S. Provisional Patent Application No. 61/653,698 and more fully explained therein, may be accomplished by numerous means, including the use of fixed bed adsorbents such as alumina, silica, ion-exchange resins, and zeolites. Particularly advantageous adsorbents are those which may be regenerated, such as by one or more techniques including (1) purge with hot $N_2$ such as at elevated temperatures such as >150° C.; (2) purge with mixture(s) of $N_2$ and at least one organic solvent such as aromatics, alcohols, ketones, etc. or at least one inorganic solvent such as water, $CO_2$, $CS_2$, etc., at temperatures such as >20° C.; (3) purge with an organic solvent such as aromatics, alcohols, ketones, etc., or an inorganic solvent such as water, $CO_2$, CS2, and the like, in either liquid phase or vapor phase at temperatures such as >20° C. followed by a $N_2$ purge at elevated temperatures such as >100° C.; (4) purge with mixture(s) of at least one organic solvent and at least one inorganic solvent at temperatures such as >25° C. followed by a $N_2$ purge at elevated temperatures such as >150° C.; or (5) purge with air, mixture of oxygen and nitrogen, steam, or mixture thereof at elevated temperatures such as >150° C.

In order to more fully understand the present invention the following detailed experiments are described. It will be understood that the experiments are not intended to be limiting but that the invention can be practiced otherwise than specifically described.

Experimental Run 1

A reactor containing 65% MCM-22/35% alumina binder catalyst was fed a xylenes stream comprising 650 ppm (wt) styrene and no heavies (A9+s) or oxygenates at 9.8 WHSV and 265 psig (1827 kPa). No hydrogen was present. Analysis of the outlet stream (such as by gas chromatography (GC)) shows high styrene conversion can be achieved at temperatures of 103-180° C. (less than 20 ppm styrene by wt, generally less than 10 ppm by wt, and often less than 5 ppm by wt). Benzene formation was below 70 ppm over a period of 760 hours. Negligible xylenes isomerization is seen at these conditions.

Experimental Run 2

The run above was continued (i.e., same reactor and catalyst) but the feed was switched to a xylenes feed containing heavies and oxygenates when the reactor temperature in the run above reached 275° C. The new feed, with heavies and oxygenates, accelerated catalyst deactivation. Similar styrene conversion was maintained by raising the reactor temperature and/or addition of hydrogen, such as 15 ppm wt. $H_2$. The reaction was stopped when the temperature reached 275° C. and the outlet styrene concentration went above about 45 ppm wt.

Table 2 compares the results at the end of Experiment Run 1 and the start of the subsequent Experiment Run 2. In the second run, there was significant xylenes isomerization and benzene formation over MCM-22 at 275° C. at SOR (start of run). Whereas in the first run, no isomerization and acceptable benzene make were seen with de-edged catalyst near EOR (end of run). "TOS" is time on stream. WHSV is weight hourly space velocity. Part per million are in weight (wppm).

TABLE 2

| Styrene Removal Run# | 1 | 2 |
|---|---|---|
| TOS (hr) | 1923 | 68 |
| Catalyst | 65% MCM-22 | 65% MCM-22 |
| Reactor Temperature (deg C.) | 275 | 275 |
| WHSV (hr$^{-1}$) | 9.8 | 9.8 |
| Feed H2 (ppm) | 15 | 15 |
| Product Styrene (ppm) | 38 | 0.42 |
| Product Benzene (ppm) | 26 | 303 |
| Product PX Selectivity (%) | 79.1 | 56.2 |

A low-reactor temperature startup can achieve adequate styrene conversion while avoiding excess xylenes isomerization and benzene yield. The temperature can be raised and/or hydrogen introduced as the catalyst ages to maintain styrene conversion while continuing to avoid excess xylenes isomerization and benzene make.

Additional examples, again not intended to be limiting, follow. These examples are representative of the removal of styrene from xylenes product of the alkylation process over a 65% MCM-22/35% alumina catalyst. Similar results would be expected for other olefinic compounds in other non-olefinic hydrocarbon streams over other solid acid catalysts under conditions other than specifically set forth herein.

Figure 3:
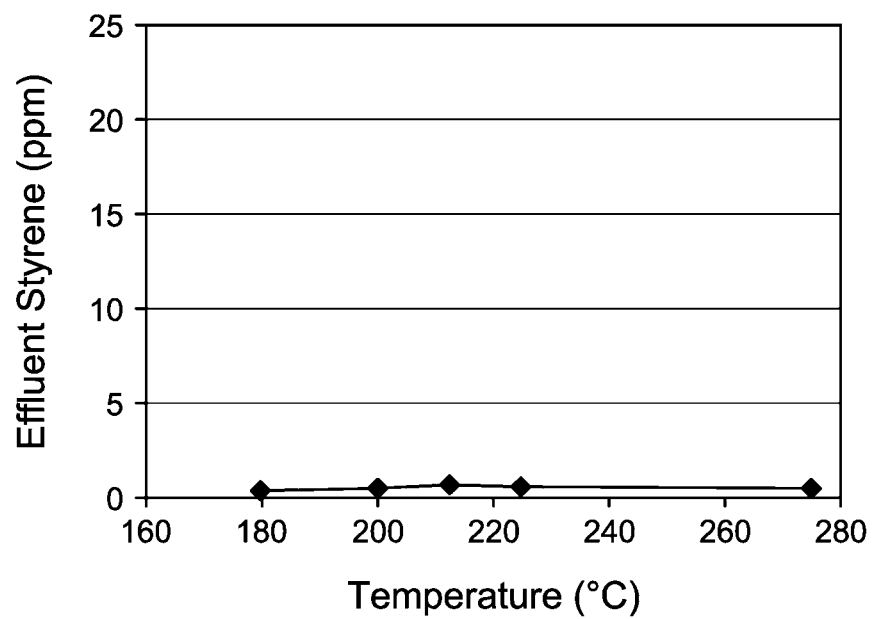
FIGS. 3-6 show experimental results on one or more embodiments of the invention.
Figure 4:
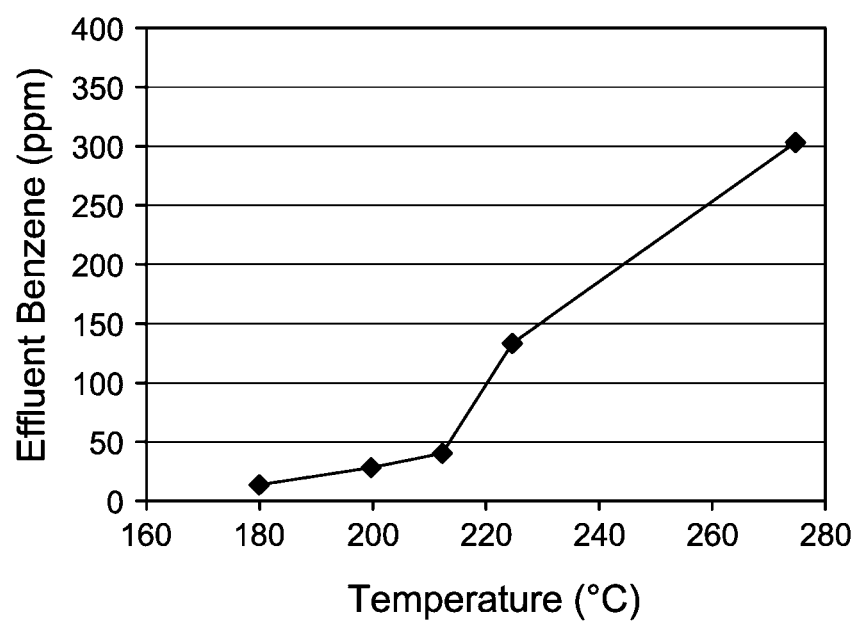
Figure 5:
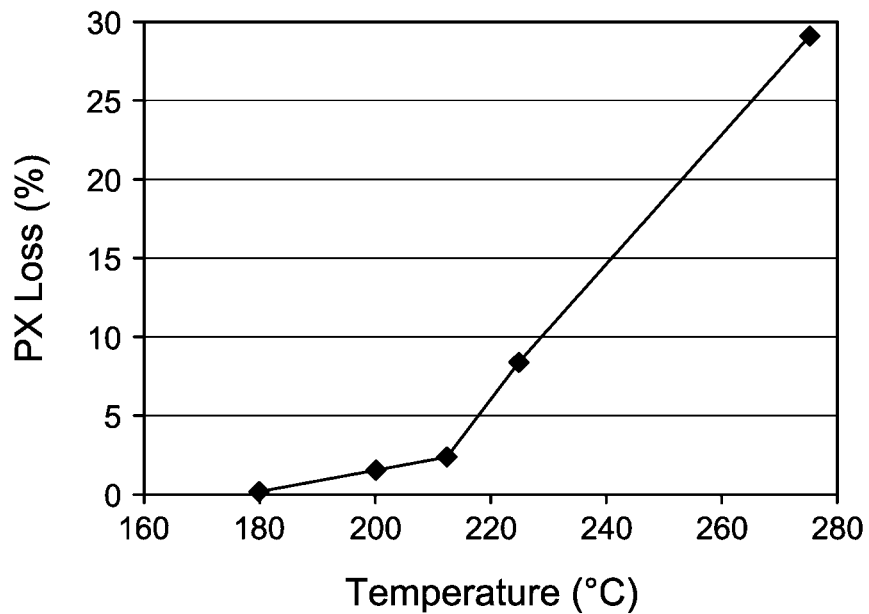

FIGS. 3, 4, and 5 show results from a laboratory experiment using a 65% MCM-22/35% alumina binder catalyst running at 2.5 WHSV and 265 psig using a xylenes feed with a greater than equilibrium (nominally 79%) concentration of para-xylene that was spiked with 650 ppm styrene. During the initial few days of operation, the reactor temperature was varied over a range of 180-275° C.

The effect of temperature on the effluent styrene concentration, the effluent benzene concentration, and paraxylene loss due to isomerization are shown in FIGS. 3, 4, and 5, respectively. The effluent styrene concentration was maintained at a consistent <1 wppm level over the entire temperature range, while the effluent benzene concentration and the paraxylene loss increased substantially as the temperature was increased. This shows that controlling the bed temperature can reduce the undesirable side reactions while maintaining good removal efficiency.

Table 3 shows results at two different WHSVs from a laboratory experiment using a 65% MCM-22/35% alumina binder catalyst running at a bed temperature of 225° C. and 265 psig using a xylenes feed with a greater than equilibrium (nominally 79%) concentration of paraxylene that was spiked with 650 wppm styrene. The reactor was at 9.8 WHSV and the flow rate was reduced to a WHSV of 2.5. The effluent styrene concentration dropped dramatically with the reduction in flow rate but the effluent benzene concentration increased only modestly and the paraxylene loss was unchanged. This shows that controlling the bed flow rate can maintain good removal efficiency without increasing the undesirable side reactions.

TABLE 3

| WHSV | 9.8 | 2.5 |
|---|---|---|
| Effluent Styrene Concentration, wppm | 50.7 | 4.1 |
| Effluent Benzene Concentration, wppm | 0.0 | 7.4 |
| Para-xylene loss, % | 0.5 | 0.5 |

Figure 6:
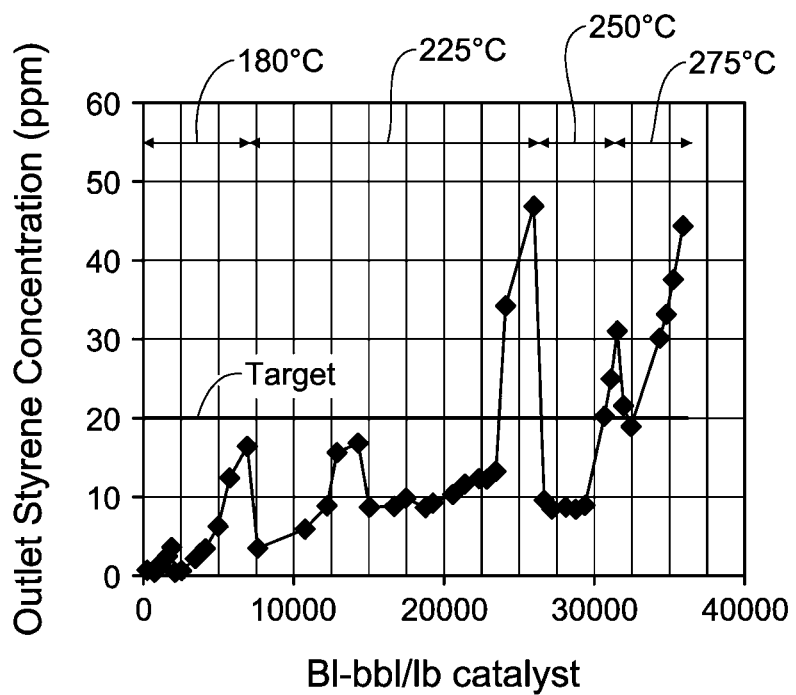

FIG. 6 shows results from another laboratory experiment using a 65% MCM-22/35% alumina binder catalyst running at 9.8 WHSV and 265 psig using a xylenes feed with a greater than equilibrium (nominally 79%) concentration of para-xylene that was spiked with 650 ppm styrene. The effluent styrene concentration is plotted in FIG. 6 as a function of the cumulative BI-bbl converterted/lb catalyst (BI/bbl is "Bromine Index/barrel", both being well-known per se). The reactor temperature in this laboratory experiment was initially at 180° C. and was increased whenever the effluent styrene approached or exceeded the target value of 20 wppm. These results show that the styrene conversion can be maintained within specification for a time by raising the reactor temperature to offset the loss of activity as the catalyst ages.

The alkylation process employed herein can employ any aromatic feedstock comprising toluene and/or benzene, although in general it is preferred that the aromatic feed contains at least 90 wt %, especially at least 99 wt %, of benzene, toluene or a mixture thereof An aromatic feed containing at least 99 wt % toluene is particularly desirable. Similarly, although the composition of the methanol-containing feed is not critical, it is generally desirable to employ feeds containing at least 90 wt %, especially at least 99 wt %, of methanol.

The catalyst employed in the alkylation process is generally a porous crystalline material and, in one preferred embodiment, is a porous crystalline material having a Diffusion Parameter for 2,2-dimethylbutane of about 0.1-15 sec-1 when measured at a temperature of 120° C. and a 2,2-dimethylbutane pressure of 60 torr (8 kPa).

As used herein, the Diffusion Parameter of a particular porous crystalline material is defined as $D/r^2 \times 106$, wherein D is the diffusion coefficient (cm2/sec) and r is the crystal radius (cm). The diffusion parameter can be derived from sorption measurements provided the assumption is made that the plane sheet model describes the diffusion process. Thus for a given sorbate loading Q, the value Q/Qeq, where Qeq is the equilibrium sorbate loading, is mathematically related to $(Dt/r^2)^{1/2}$ where t is the time (sec) required to reach the sorbate loading Q. Graphical solutions for the plane sheet model are given by J. Crank in "The Mathematics of Diffusion", Oxford University Press, Ely House, London, 1967.

The porous crystalline material is preferably a medium-pore size aluminosilicate zeolite. Medium pore zeolites are generally defined as those having a pore size of about 5 to about 7 Angstroms, such that the zeolite freely sorbs molecules such as n-hexane, 3-methylpentane, benzene and p-xylene. Another common definition for medium pore zeolites involves the Constraint Index test which is described in U.S. Pat. No. 4,016,218, which is incorporated herein by reference. In this case, medium pore zeolites have a Constraint Index of about 1-12, as measured on the zeolite alone without the introduction of oxide modifiers and prior to any steaming to adjust the diffusivity of the catalyst. In addition to the medium-pore size aluminosilicate zeolites, other medium pore acidic metallosilicates, such as silicoaluminophosphates (SAPOs), can be used in the present process.

Particular examples of suitable medium pore zeolites include ZSM-5, ZSM-11, ZSM-12, ZSM-22, ZSM-23, ZSM-35, and ZSM-48, with ZSM-5 and ZSM-11 being particularly preferred. In one embodiment, the zeolite employed in the process of the invention is ZSM-5 having a silica to alumina molar ratio of at least 250, as measured prior to any treatment of the zeolite to adjust its diffusivity.

Zeolite ZSM-5 and the conventional preparation thereof are described in U.S. Pat. No. 3,702,886. Zeolite ZSM-11 and the conventional preparation thereof, are described in U.S. Pat. No. 3,709,979. Zeolite ZSM-12 and the conventional preparation thereof, are described in U.S. Pat. No. 3,832,449. Zeolite ZSM-23 and the conventional preparation thereof, are described in U.S. Pat. No. 4,076,842. Zeolite ZSM-35 and the conventional preparation thereof, are described in U.S. Pat. No. 4,016,245. ZSM-48 and the conventional preparation thereof, are taught by U.S. Pat. No. 4,375,573. The entire disclosures of these U.S. patents are incorporated herein by reference.

The medium pore zeolites described above are preferred for the present process since the size and shape of their pores favor the production of p-xylene over the other xylene isomers. However, conventional forms of these zeolites have Diffusion Parameter values in excess of the 0.1-15 sec-1 range desired for the present process. Nevertheless, the required diffusivity can be achieved by severely steaming the zeolite so as to effect a controlled reduction in the micropore volume of the catalyst to not less than 50%, and preferably 50-90%, of that of the unsteamed catalyst. Reduction in micropore volume is monitored by measuring the n-hexane adsorption capacity of the zeolite, before and after steaming, at 90° C. and 75 torr n-hexane pressure.

Steaming to achieve the desired reduction in the micropore volume of the porous crystalline material can be effected by heating the material in the presence of steam at a temperature of at least about 950° C., preferably about 950 to about 1075° C., and most preferably about 1000 to about 1050° C. for about 10 minutes to about 10 hours, preferably from 30 minutes to 5 hours.

To effect the desired controlled reduction in diffusivity and micropore volume, it may be desirable to combine the porous crystalline material, prior to steaming, with at least one oxide modifier, preferably selected from oxides of the elements of Groups IIA, IIIA, IIIB, IVA, VA, VB and VIA of the Periodic Table (IUPAC version). Conveniently, said at least one oxide modifier is selected from oxides of boron, magnesium, calcium, lanthanum and preferably phosphorus. In some cases, it may be desirable to combine the porous crystalline material with more than one oxide modifier, for example a combination of phosphorus with calcium and/or magnesium, since in this way it may be possible to reduce the steaming severity needed to achieve a target diffusivity value. The total amount of oxide modifier present in the catalyst, as measured on an elemental basis, may be between about 0.05 and about 20 wt %, such as between about 0.1 and about 10 wt %, based on the weight of the final catalyst.

Where the modifier includes phosphorus, incorporation of modifier in the alkylation catalyst is conveniently achieved by the methods described in U.S. Pat. Nos. 4,356,338; 5,110,776; 5,231,064; and 5,348,643; the entire disclosures of which are incorporated herein by reference. Treatment with phosphorus-containing compounds can readily be accomplished by contacting the porous crystalline material, either alone or in combination with a binder or matrix material, with a solution of an appropriate phosphorus compound, followed by drying and calcining to convert the phosphorus to its oxide form. Contact with the phosphorus-containing compound is generally conducted at a temperature of about 25° C. and about 125° C. for a time between about 15 minutes and about 20 hours. The concentration of the phosphorus in the contact mixture may be between about 0.01 and about 30 wt %.

Representative phosphorus-containing compounds which may be used to incorporate a phosphorus oxide modifier into the catalyst of the invention include derivatives of groups represented by PX3, RPX2, R2PX, R3P, X3PO, (XO)3PO, (XO)3P, R3P=O, R3P=S, RPO2, RPS2, RP(O)(OX)2, RP(S)(SX)2, R2P(O)OX, R2P(S)SX, RP(OX)2, RP(SX)2, ROP(OX)2, RSP(SX)2, (RS)2PSP(SR)2, and (RO)2POP(OR)2, where R is an alkyl or aryl, such as phenyl radical, and X is hydrogen, R, or halide. These compounds include primary, RPH2, secondary, R2PH, and tertiary, R3P, phosphines such as butyl phosphine, the tertiary phosphine oxides, R3PO, such as tributyl phosphine oxide, the tertiary phosphine sulfides, R3PS, the primary, RP(O)(OX)2, and secondary, R2P(O)OX, phosphonic acids such as benzene phosphonic acid, the corresponding sulfur derivatives such as RP(S)(SX)2 and R2P(S)SX, the esters of the phosphonic acids such as dialkyl phosphonate, (RO)2P(O)H, dialkyl alkyl phosphonates, (RO)2P(O)R, and alkyl dialkylphosphinates, (RO)P(O)R2; phosphinous acids, R2PDX, such as diethylphosphinous acid, primary, (RO)P(OX)2, secondary, (RO)2PDX, and tertiary, (RO)3P, phosphites, and esters thereof such as the monopropyl ester, alkyl dialkylphosphinites, (RO)PR2, and dialkyl alkyphosphinite, (RO)2PR, esters. Corresponding sulfur derivatives may also be employed including (RS)2P(S)H, (RS)2P(S)R, (RS)P(S)R2, R2PSX, (RS)P(SX)2, (RS)2PSX, (RS)3P, (RS)PR2, and (RS)2PR. Examples of phosphite esters include trimethylphosphite, triethylphosphite, diisopropylphosphite, butylphosphite, and pyrophosphites such as tetraethylpyrophosphite. The alkyl groups in the mentioned compounds preferably contain one to four carbon atoms.

Other suitable phosphorus-containing compounds include ammonium hydrogen phosphate, the phosphorus halides such as phosphorus trichloride, bromide, and iodide, alkyl phosphorodichloridites, (RO)PCl2, dialkylphosphoro-chloridites, (RO)2PCl, dialkylphosphinochloridites, R2PCl, alkyl alkylphosphonochloridates, (RO)(R)P(O)Cl, dialkyl phosphinochloridates, R2P(O)Cl, and RP(O)Cl2. Applicable corresponding sulfur derivatives include (RS)PCl2, (RS)2PCl, (RS)(R)P(S)Cl, and R2P(S)Cl.

Particular phosphorus-containing compounds include ammonium phosphate, ammonium dihydrogen phosphate, diammonium hydrogen phosphate, diphenyl phosphine chloride, trimethylphosphite, phosphorus trichloride, phosphoric acid, phenyl phosphine oxychloride, trimethylphosphate, diphenyl phosphinous acid, diphenyl phosphinic acid, diethylchlorothiophosphate, methyl acid phosphate, and other alcohol-P2O5 reaction products.

Representative boron-containing compounds which may be used to incorporate a boron oxide modifier into the catalyst of the invention include boric acid, trimethylborate, boron oxide, boron sulfide, boron hydride, butylboron dimethoxide, butylboric acid, dimethylboric anhydride, hexamethylborazine, phenyl boric acid, triethylborane, diborane and triphenyl boron.

Representative magnesium-containing compounds include magnesium acetate, magnesium nitrate, magnesium benzoate, magnesium propionate, magnesium 2-ethylhexoate, magnesium carbonate, magnesium formate, magnesium oxylate, magnesium bromide, magnesium hydride, magnesium lactate, magnesium laurate, magnesium oleate, magnesium palmitate, magnesium salicylate, magnesium stearate and magnesium sulfide.

Representative calcium-containing compounds include calcium acetate, calcium acetylacetonate, calcium carbonate, calcium chloride, calcium methoxide, calcium naphthenate, calcium nitrate, calcium phosphate, calcium stearate and calcium sulfate.

Representative lanthanum-containing compounds include lanthanum acetate, lanthanum acetylacetonate, lanthanum carbonate, lanthanum chloride, lanthanum hydroxide, lanthanum nitrate, lanthanum phosphate and lanthanum sulfate.

The porous crystalline material employed in the process of the invention may be combined with a variety of binder or matrix materials resistant to the temperatures and other conditions employed in the process. Such materials include active and inactive materials such as clays, silica and/or metal oxides such as alumina. The latter may be either naturally occurring or in the form of gelatinous precipitates or gels including mixtures of silica and metal oxides. Use of a material which is active, tends to change the conversion and/or selectivity of the catalyst and hence is generally not preferred. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the porous crystalline material include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the porous crystalline material can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia, and silica-magnesia-zirconia.

The relative proportions of porous crystalline material and inorganic oxide matrix vary widely, with the content of the former ranging from about 1 to about 90% by weight and more usually, particularly when the composite is prepared in the form of beads, in the range of about 2 to about 80 wt % of the composite.

The alkylation process can be conducted in any known reaction vessel but generally the methanol and aromatic feeds are contacted with the catalyst described above with the catalyst particles being disposed in one or more fluidized beds. Each of the methanol and aromatic feeds can be injected into the fluidized catalyst in a single stage. However, in one embodiment, the methanol feed is injected in stages into the fluidized catalyst at one or more locations downstream from the location of the injection of the aromatic reactant into the fluidized catalyst. For example, the aromatic feed can be injected into a lower portion of a single vertical fluidized bed of catalyst, with the methanol being injected into the bed at a plurality of vertically spaced intermediate portions of the bed and the product being removed from the top of the bed.

Alternatively, the catalyst can be disposed in a plurality of vertically spaced catalyst beds, with the aromatic feed being injected into a lower portion of the first fluidized bed and part of the methanol being injected into an intermediate portion of the first bed and part of the methanol being injected into or between adjacent downstream catalyst beds.

The conditions employed in the alkylation stage of the present process are not narrowly constrained but, in the case of the methylation of toluene, generally include the following ranges: (a) temperature between about 500 and about 700° C., such as between about 500 and about 600° C.; (b) pressure of between about 1 atmosphere and about 1000 psig (between about 100 and about 7000 kPa), such as between about 10 psig and about 200 psig (between about 170 and about 1480 kPa); (c) moles toluene/moles methanol (in the reactor charge) of at least about 0.2, such as from about 0.2 to about 20; and (d) a weight hourly space velocity ("WHSV") for total hydrocarbon feed to the reactor(s) of about 0.2 to about 1000, such as about 0.5 to about 500 for the aromatic reactant, and about 0.01 to about 100 for the combined methanol reagent stage flows, based on total catalyst in the reactor(s).

The product of the reaction between the methanol and the aromatic feed is a gaseous effluent comprising para-xylene and other xylene isomers, water vapor, unreacted toluene and/or benzene, unreacted methanol, phenolic impurities, light olefins and other light gas by-products, and generally some C9+ aromatic by-products. In addition, where the process is conducted in a fluidized catalyst bed, the effluent will contain some entrained solid catalyst and catalyst fines. Thus, the gaseous effluent leaving the (final) fluidized bed reactor is generally passed through an integral cyclone separator to remove some of the entrained catalyst solids and return them to the alkylation reactor.

The product effluent leaves the alkylation reactor system at a high temperature, typically between about 500 and about 600° C. and initially may be passed through a heat exchanger so that the waste heat in the effluent stream may be recovered and used to heat other process stream(s). It is, however, preferred that any initial cooling of the product stream is limited so as to keep the effluent vapors well above the dew point, typically about 240° F. (116° C.).

Following further cooling, the effluent vapor stream is fed to a separation system, which may comprise one or more fractionation columns, where the unreacted methanol and aromatics are recovered and recycled to the alkylation step, the light and heavy hydrocarbons are removed and the remainder of effluent is separated into a liquid organic phase rich in xylene and a waste water stream. Part of the phenolic impurities are concentrated in the xylene-rich organic phase and part are dissolved in the waste water stream making the waste water stream acidic.

Typically, the phenolic impurities include phenol, methyl phenols and dimethyl phenols and are present in the xylene filtrate in an amount from about 0.2 ppmw to about 1000 ppmw of phenol, from about 0.2 ppmw to about 1000 ppmw of methyl phenols and from about 0.5 ppmw to about 1000 ppmw of dimethyl phenols.

The present invention can be integrated with other systems using toluene and benzene streams, such as selective disproportionation of toluene and/or transalkylation of toluene and aromatic C9+ species.

The invention has been described above with reference to numerous embodiments and specific examples. Many variations will suggest themselves to those skilled in this art in light of the above detailed description.

Trade names used herein are indicated by a TM symbol or ® symbol, indicating that the names may be protected by certain trademark rights, e.g., they may be registered trademarks in various jurisdictions. All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

What is claimed is:

1. An apparatus comprising an alkylation reactor fluidly connected with a purification system comprising at least one apparatus adapted for the selective removal of styrene by contact of a process stream with at least one material selected from MWW molecular sieves, clays, and mixtures thereof, to provide a product stream without significant production of benzene and without significant loss of paraxylene by isomerization, said at least one apparatus adapted for the removal of styrene fluidly connect to and upstream of an apparatus for the selective removal of paraxylene from a process stream, wherein the selective removal of styrene causes less than 5 wt % of paraxylene to be lost to isomerization by said contact, and wherein said contact comprises initially contacting said process stream with said at least one material at a temperature of about 100° C. to about 180° C. to effectively remove styrene until paraxylene lost by isomerization is less than 5 wt % and subsequently raising said temperature to about 275° C. in a step-wise manner while maintaining paraxylene lost by isomerization to less than 5 wt %.

2. The apparatus according to claim 1, wherein said purification system comprises a vessel containing a material selected from MCM-22, MCM-49, and MCM-56 molecular sieves, acid-treated clays, and mixtures thereof.

3. The apparatus according to claim 2, further comprising a liquid isomerization unit, a vapor phase isomerization unit, or a combination thereof.

4. The apparatus according to claim 3, further characterized by being integrated by fluid connection and/or heat exchange to a system adapted for at least one of the processes selected from: (i) transalkylation of an aromatic species; (ii) disproportionation of an aromatic species; and (iii) disproportionation and transalkylation of an aromatic species; wherein said disproportionation may be selective disproportionation or non-selective disproportionation.

\* \* \* \* \*